United States Patent
Zysk et al.

(10) Patent No.: US 12,402,922 B2
(45) Date of Patent: Sep. 2, 2025

(54) BONE PLATE WITH LENGTH ADJUSTING ELONGATE HOLE, AND CORRESPONDING METHODS OF USE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Adam Zysk, Germantown, TN (US); Kohsuke Watanabe, Memphis, TN (US); William M. Ricci, New York, NY (US); Samir Mehta, Haddonfield, NJ (US); Nicholas S. Ritchey, Collierville, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 313 days.

(21) Appl. No.: 17/917,978

(22) PCT Filed: Apr. 15, 2021

(86) PCT No.: PCT/US2021/027519
§ 371 (c)(1),
(2) Date: Oct. 10, 2022

(87) PCT Pub. No.: WO2021/221920
PCT Pub. Date: Nov. 4, 2021

(65) Prior Publication Data
US 2023/0142959 A1    May 11, 2023

Related U.S. Application Data

(60) Provisional application No. 63/017,062, filed on Apr. 29, 2020.

(51) Int. Cl.
*A61B 17/80* (2006.01)

(52) U.S. Cl.
CPC ...... *A61B 17/8014* (2013.01); *A61B 17/8057* (2013.01)

(58) Field of Classification Search
CPC .................................................. A61B 17/8014
See application file for complete search history.

(56) References Cited

U.S. PATENT DOCUMENTS

| 7,537,604 B2 | 5/2009 | Huebner |
| 2009/0254126 A1 | 10/2009 | Orbay et al. |

(Continued)

OTHER PUBLICATIONS

International Search Report and Written Opinion mailed Jul. 20, 2021, for International Patent Application No. PCT/US2021/027519 (13 pages).

(Continued)

*Primary Examiner* — Olivia C Chang
(74) *Attorney, Agent, or Firm* — KDW Firm PLLC

(57) ABSTRACT

A bone plate incorporating a length adjusting elongate hole formed in a shaft portion thereof, along with corresponding methods of use. In one embodiment, the length adjusting elongate hole is configured to receive one or more bone fixation devices (e.g., bone screws). In use, the bone fixation device positioned within the length adjusting elongate hole may be partially loosened, without removal, to enable the patient's bone to be adjusted (e.g., loosening the bone fixation device within the length adjusting elongate hole allows the surgeon to adjust the position of the patient's bone, and hence the bone fixation device coupled thereto, relative to the bone plate). Once properly adjusted, the bone fixation device positioned within the length adjusting elongate hole may be retightened. In various embodiments, the length adjusting elongate hole is configured so that, in use, (Continued)

each of the plurality of bone fixation openings remains available to a surgeon.

13 Claims, 5 Drawing Sheets

(56) References Cited

U.S. PATENT DOCUMENTS

| | | |
|---|---|---|
| 2011/0264149 A1 | 10/2011 | Pappalardo et al. |
| 2012/0123484 A1* | 5/2012 | Lietz .................... A61B 17/809 |
| | | 606/291 |
| 2015/0257802 A1 | 9/2015 | Wolf et al. |
| 2018/0049782 A1 | 2/2018 | Gahman et al. |
| 2018/0310972 A1* | 11/2018 | Anding .............. A61B 17/8605 |
| 2020/0323570 A1 | 10/2020 | Austin et al. |
| 2022/0233222 A1* | 7/2022 | Papannagari ...... A61B 17/8052 |

OTHER PUBLICATIONS

European Patent Office, Communication Pursuant to Article 94(3) EPC, dated Aug. 20, 2024, 6 pages.

* cited by examiner

BONE PLATE WITH LENGTH ADJUSTING ELONGATE HOLE, AND CORRESPONDING METHODS OF USE

CROSS-REFERENCE TO RELATED APPLICATIONS

This application is a National Phase filing of International Application No. PCT/US2021/027519, filed Apr. 15, 2021, which application is a non-provisional of, and claims the benefit of the filing date of, U.S. provisional patent application No. 63/017,062, filed Apr. 29, 2020, entitled "Bone Plate with Length Adjusting Elongate Hole," the entirety of each application is incorporated by reference herein.

FIELD OF THE DISCLOSURE

The present disclosure is directed to orthopedic implants (e.g., bone plates) for coupling to one or more patient's bones, bone portions, bone fragments, etc., and more specifically to bone plates for enabling surgeons to adjust a length of a fractured bone without removal of the bone plate (e.g., decoupling both ends of the bone plate from the patient's underlying bone) and/or without sacrificing (e.g., eliminating, preventing use, etc.) any bone fixation openings.

BACKGROUND OF THE DISCLOSURE

Bone fractures are often repaired by securing an orthopedic implant or device to one or more patient's bone(s), bone portions, bone fragments, etc. (used interchangeably without the intent to limit). For example, it is not uncommon for a patient to receive a bone plate to repair one or more fractures in a patient's bone.

During the treatment period, for one or more reasons, a surgeon may need to adjust the length of the fractured bone. However adjusting the length of a fractured bone that is coupled to a bone plate presents numerous challenges. For example, it is not uncommon for surgeons to fix or secure one end of the bone plate to the patient's bone such as, for example, to fix the bone plate to a proximal or distal segment of the fracture, while the opposite end of the bone plate may remain free. For example, the surgeon may place provisional fixation pins in the unfixed region of the bone plate. In use, the provisional fixation pins may be positioned along an outside of the bone plate to create a constrained path for the plate to translate. The surgeon may then use a series of bone clamps or compression screws in an attempt to keep the bone plate positioned on the patient's bone while enabling the bone plate to translate. In this manner, the surgeon can achieve the desired position, limb length, and/or flexion/extension.

Thus arranged, enabling translation of the bone plate requires one portion or end of the bone plate to remove fixation (e.g., to be decoupled from the patient's fractured bone), which may disrupt fracture reduction in close proximity (e.g. comminution, setting of flexion/extension), or cause the bone plate to move in an undesired manner. In addition, enabling translation of the bone plate requires additional instrumentation such as, for example, bone clamps, articulated tensioning devices, etc. Moreover, the incorporation of cortical bone screws to compress the bone plate to the patient's bone may prevent, or at least inhibit, the surgeon from utilizing locking screws if the new screw hole overlaps the screw hole created to provisionally fix the bone plate to the patient's bone. As such, one or more screw holes may be sacrificed (e.g., surgeon may be prevented from using the screw hole during the surgical procedure).

Thus, it would be beneficial to provide a bone plate and corresponding methods of use that is arranged and configured to enable a length of the patient's bone to be adjusted without requiring the bone plate to be decoupled from the patient's bone and/or require any additional instrumentation. In addition, it would be beneficial to provide a bone plate that is arranged and configured to enable a length of the patient's bone to be adjusted without sacrificing any bone fixation openings (e.g., bone plate is arranged and configured to enable length adjustment without reducing the number of bone fixation openings provided in the bone plate and/or their availability to the surgeon during the surgical procedure).

It is with respect to these and other considerations that the present disclosure may be useful.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, a bone plate is disclosed. The bone plate includes a shaft portion and a length adjusting elongate hole formed in the shaft portion. The shaft portion includes a central longitudinal axis, an upper surface, a bottom surface, and a plurality of bone fixation openings extending between the upper and bottom surfaces, each of the plurality of bone fixation openings being arranged and configured to receive a bone fixation device for coupling the bone plate to a patient's bone. The length adjusting elongate hole includes a central longitudinal axis. In use, the length adjusting elongate hole is arranged and configured to enable a length of the patient's bone to be adjusted without requiring the bone plate to be completely decoupled from the patient's bone. The length adjusting hole is one of: (i) the central longitudinal axis of the length adjusting hole being spaced offset from the central longitudinal axis of the shaft portion, the length adjusting elongate hole positioned adjacent to and offset from one of the plurality of bone fixation openings; or (ii) the central longitudinal axis of the length adjusting hole being aligned with the central longitudinal axis of the shaft portion, the length adjusting elongate hole extending between adjacent bone fixation openings formed in the shaft portion of the bone plate, the length adjusting elongate hole being in communication with the adjacent bone fixation openings.

In one embodiment, the central longitudinal axis of the length adjusting hole is aligned with the central longitudinal axis of the shaft portion, the length adjusting elongate hole extending between adjacent bone fixation openings formed in the shaft portion of the bone plate so that the length adjusting elongate hole is in communication with the adjacent bone fixation openings, the adjacent bone fixation openings are locking screw openings.

In one embodiment, the locking screw openings are positioned on either side of the central longitudinal axis of the shaft portion.

In one embodiment, the length adjusting elongate hole includes a length at least twice a diameter of a bone fixation opening.

In one embodiment, the length adjusting hole includes a dished or recessed region arranged and configured to enable a bone fixation device to be recessed relative to the upper surface of the bone plate.

In one embodiment, the length adjusting elongate hole includes a recess portion on the bottom surface.

In one embodiment, a bone plate is disclosed. The bone plate includes a shaft portion and a length adjusting elongate hole formed in the shaft portion. The shaft portion includes an upper surface, a bottom surface, and a plurality of bone fixation openings extending between the upper and bottom surfaces, each of the plurality of bone fixation openings being arranged and configured to receive a bone fixation device for coupling the bone plate to a patient's bone. The length adjusting elongate hole extends between adjacent bone fixation openings formed in the shaft portion of the bone plate so that the length adjusting elongate hole is in communication with the adjacent bone fixation openings, the length adjusting elongate hole being arranged and configured to enable a length of the patient's bone to be adjusted without requiring the bone plate to be decoupled from the patient's bone.

In one embodiment, the length adjusting hole includes a central longitudinal axis aligned with a central longitudinal axis of the shaft portion.

In one embodiment, the adjacent bone fixation openings are locking screw openings.

In one embodiment, the locking screw openings are positioned on either side of the central longitudinal axis of the shaft portion.

In one embodiment, the length adjusting elongate hole is arranged and configured so that, in use, each of the plurality of bone fixation openings remains available to a surgeon.

In one embodiment, a method of fracture reduction is disclosed. The method utilizing a bone plate with a length adjusting elongate hole formed in a shaft portion of the bone plate. The method comprising coupling a portion of the bone plate to a patient's bone utilizing one or more bone fixation devices; inserting a bone fixation device into the length adjusting elongate hole, the bone fixation device being positioned within one side of the length adjusting elongate hole; reducing an amount of provisional compression from the bone fixation device; adjusting a length of the patient's bone; compressing the bone plate against the patient's bone using the previously inserted bone fixation device; and inserting a locking screw into an adjacent locking screw opening formed in the bone plate.

In one embodiment, the bone plate is provisionally held against the patient's bone during inserting the bone fixation device into the length adjusting elongate hole.

In one embodiment, adjusting a length of the patient's bone comprises reducing or compressing the patient's bone.

In one embodiment, adjusting a length of the patient's bone comprises lengthening or distracting the patient's bone.

In one embodiment, the method further comprises reducing the patient's bone.

In one embodiment, reducing the patient's bone is accomplished prior to coupling a portion of the bone plate to the patient's bone.

Embodiments of the present disclosure provide numerous advantages. For example, by incorporating a length adjusting elongate hole, surgeons are able to facilitate length adjustment without losing fracture reduction, surgeons are able to maintain desired plate placement relative to the patient's bone because the length adjusting elongate hole constrains translation of the bone plate without the need for additional instrumentation, and/or surgeons are able to facilitate length adjustment through the bone plate without requiring a plurality of additional instrumentation to adjust length. In addition, the positioning and arrangement of the length adjusting elongate hole does not eliminate, remove, or prevent incorporation of any bone fixation openings in the plate nor their availability during the surgical procedure thereby providing the surgeon with additional options.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
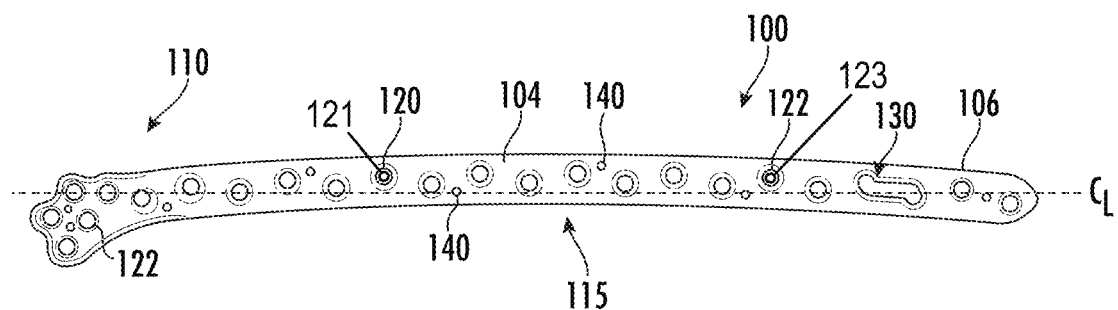
FIG. 1 illustrates a top view of an example embodiment of a bone plate in accordance with one or more features of the present disclosure.
Figure 2:
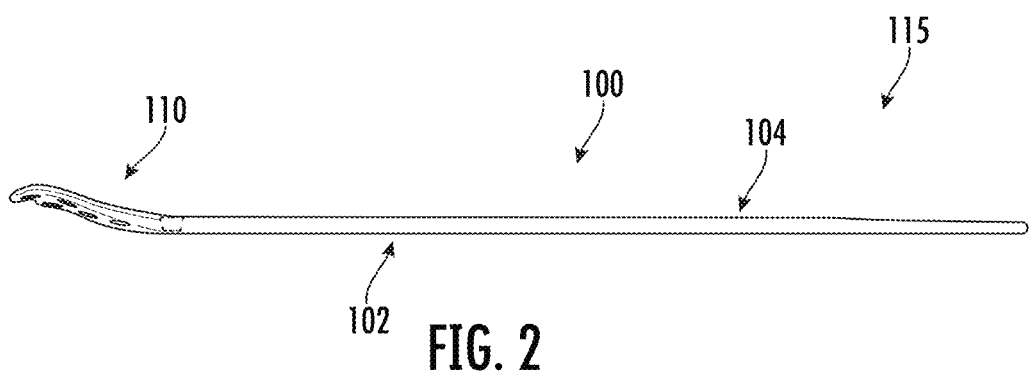
FIG. 2 illustrates a side view of the bone plate shown in FIG. 1.
Figure 3:
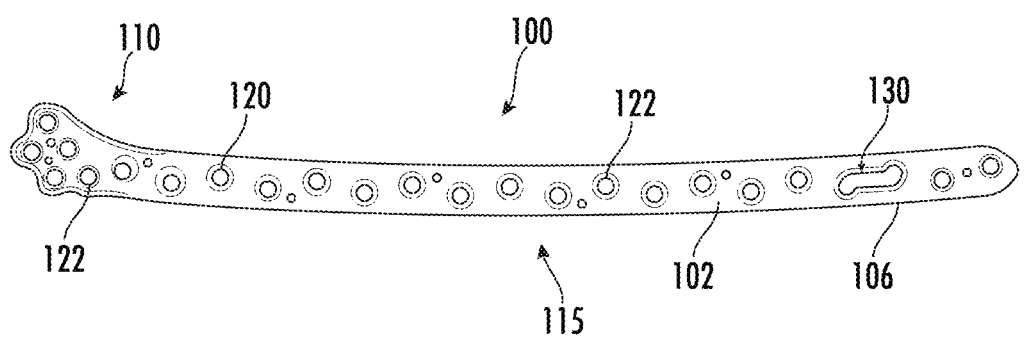
FIG. 3 illustrates a bottom view of the bone plate shown in FIG. 1.

The drawings are not necessarily to scale. The drawings are merely representations, not intended to portray specific parameters of the disclosure. The drawings are intended to depict various embodiments of the disclosure, and therefore are not be considered as limiting in scope. In the drawings, like numbering represents like elements throughout unless otherwise noted.

DETAILED DESCRIPTION

Various features or the like of orthopedic bone plates will now be described more fully hereinafter with reference to the accompanying drawings, in which one or more features of the bone plates will be shown and described. It should be appreciated that the various features may be used independently of, or in combination, with each other. It will be appreciated that a bone plate as disclosed herein may be embodied in many different forms and should not be construed as being limited to the embodiments set forth herein.

Rather, these embodiments are provided so that this disclosure will convey certain features of the bone plate to those skilled in the art.

As will be described herein, the present disclosure discloses a bone plate including one or more features that may be used in combination or singularly. As will be disclosed herein, the bone plates include one or more features designed and configured to provide increased flexibility in enabling a surgeon to position and secure a bone plate across a fracture in a patient's bone. For example, in one embodiment, the bone plate is arranged and configured to enable a length of the underlying fractured bone to be adjusted (e.g., lengthened or reduced) without requiring the bone plate to be completely decoupled at one end from the patient's bone. In various embodiments, the bone plate incorporates a length adjusting elongate hole arranged and configured to enable a length of the underlying fractured bone to be adjusted without sacrificing or eliminating the incorporation of any bone fixation openings or their availability of use during the surgical procedure.

As will be described herein, the bone plate may have various shapes and/or configurations. It should be appreciated that the bone plate may be provided in any suitable shape and/or configuration, which, as will be appreciated by one of ordinary skill in the art, may be dependent on the location and type of patient's bone being fixed. For example, a bone plate may include a bone conforming arcuate surface. In addition, the bone plate may be arranged and configured to span, contact, etc. a distal femur, a proximal femur, a distal tibia, a proximal tibia, a proximal humerus, a distal humerus, a fibula, an ulna, a radius, a distal radius, bones of the foot, or bones of the hand, shaft fractures on long bones, etc.

In addition, the bone plate, may include any now known or hereafter developed additional features such as, for example, one or more openings or slots designed to receive, for example, surgical implantation tools, different fasteners (e.g., non-locking fasteners), or the like.

The bone plate may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body.

In use, the bone plate may be coupled, secured, fixed, etc. to a patient's bone using one or more bone fixation devices such as, for example, provisional fixation pins, bone screws (e.g., locking and/or non-locking), fasteners, or other compression devices. In some embodiments, the bone fixation device may be manufactured from the same material as the bone plate. In other embodiments, the bone fixation device may be manufactured from a different material as compared to the bone plate.

The bone fixation device can be any type of bone fixation device now known or hereafter developed. For example, the bone fixation device may be in the form of a screw and may include any type of external thread including standard or non-standard threads. For example, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking screws, the head portion of the screw can include any surface that will engage with and seat within a locking screw opening formed in the bone plates. For example, the head portion can include threads. Alternatively, the head portion can include a series of dimples, ridges, bumps, textured areas, or any other surface that can secure the screw.

The bone fixation device may be any typical fastener or screw, made out of any appropriate material. The bone fixation device may include a bore for receiving a driver in order to drive the bone fixation device through the bone plate and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the bone fixation device through the bone plate and into the patient's bone.

The shaft of the bone fixation device may be fully threaded, partially threaded, or a helical blade, and/or may include one or more tacks, deployable talons, expandable elements, or any feature that allows the shaft to engage the patient's bone. It is also possible that shaft be non-threaded so that the bone fixation device takes the form of a peg or a pin. This alternative implementation may be preferred in certain procedures where, for instance, the main goal is to prevent tilting of a bone segment or in procedures where there is no concern of the bone fixation device pulling out from the patient's bone and hence no need for the shaft to be threaded or otherwise configured to engage the patient's bone. The end of the shaft may be a self-tapping or self-drilling tip.

In any event, as will be readily apparent from the remaining disclosure, the focus of the present disclosure is on example embodiments of bone plates including one or more features arranged and configured to provide increased flexibility for positioning and securing the bone plate. Thus, it should be appreciated that the present disclosure should not be limited to any particular configuration of bone plate and/or bone fixation device unless specifically claimed.

In accordance with one or more features of the present disclosure, a bone plate may incorporate a length adjusting elongate hole of varying lengths in a shaft portion of the bone plate. In use, the length adjusting elongate hole may be sized to accept a bone fixation device. In one embodiment, the elongate hole may be positioned adjacent to and offset from one or more bone fixation openings formed in the bone plate. Alternatively, and/or in addition, the length adjusting elongate hole may be arranged and configured to communicate with adjacent pairs of bone fixation openings so that the length adjusting elongate hole traverses adjacent bone fixation openings (e.g., the length adjusting elongate hole intersects adjacent locking screw openings formed in the bone plate).

As will be described in greater detail below, in some embodiments, the length adjusting elongate hole is arranged and configured to accept one or more bone fixation devices so that a bone fixation device can be locked within the elongate hole at any position along a length of the elongate hole. In addition, and/or alternatively, in some embodiments, the length adjusting elongate hole may include a dished region arranged and configured to enable a bone fixation device such as, for example, a cortical bone screw, to be recessed within the shaft portion of the bone plate.

As will be described in greater detail below, a method of fracture reduction utilizing a bone plate with a length adjusting elongate hole formed in the shaft portion of the bone plate is also disclosed. In one embodiment, the method includes the steps of: (1) reducing and fixing (e.g., coupling, fixing, securing, etc.) one portion of the bone plate to a patient's bone; (2) inserting a bone fixation device (e.g., a cortical bone screw) into the length adjusting elongate hole, the bone screw being positioned within one or a first side of the length adjusting elongate hole, the bone plate being provisionally held against the patient's bone; (3) reducing the amount of provisional compression from the bone fixation device and adjusting the length (compression or distraction) of the patient's bone; (4) compressing the bone plate against the patient's bone using the previously inserted bone fixation device; and (5) inserting a bone fixation device (e.g., a locking screw) into either of the adjacent bone fixation openings (e.g., locking screw openings) formed in the bone plate.

In use, by incorporating a length adjusting elongate hole, surgeons are able to facilitate length adjustment without losing fracture reduction. In addition, and/or alternatively, surgeons can maintain desired plate placement relative to the patient's bone because the length adjusting elongate hole constrains translation of the bone plate without the need for additional instrumentation. In addition, and/or alternatively, surgeons can facilitate length adjustment utilizing the bone plate without needing a plurality of additional instrumentation to adjust length. In addition, and/or alternatively, the bone plate facilitates length adjustment without sacrificing or eliminating any bone fixation openings.

Referring to FIGS. 1-4, various embodiments of a bone plate 100 having various lengths for repairing fractures in a patient's bone are disclosed. As will be described herein, the bone plates 100 may be in the form of a distal femur plate. That is, the bone plate 100 may be arranged and configured for positioning adjacent to a distal femur of a patient. However, as previously mentioned, it should be appreciated that the bone plate 100 may have various shapes and/or configurations and may be provided in any suitable shape and/or configuration, which, as will be appreciated by one of ordinary skill in the art, may be dependent on the location and type of patient's bone being fixed. For example, the bone plate 100 may be arranged and configured to span, contact, etc. a distal femur, a proximal femur, a distal tibia, a proximal tibia, a proximal humerus, a distal humerus, a fibula, an ulna, a radius, a distal radius, bones of the foot, or bones of the hand, shaft fractures on long bones, etc.

In accordance with one or more features of the present disclosure, as will be described herein, the bone plate 100 includes one or more features so that the bone plate 100 facilitates positioning and securement to a patient's bone (e.g., patient's distal femur).

As shown, the bone plate 100 may include an underside or bone facing bottom surface 102 and an upper surface 104. In addition, the bone plate 100 may include a head portion 110 and a shaft portion 115 having a central longitudinal axis CL. Moreover, the bone plate 100 includes a plurality of bone fixation openings 120 formed therein for receiving a plurality of bone fixation devices 121 for coupling the bone plate 100 to the patient's bone. In use, the bone fixation openings 120 may be in the form of a locking screw opening 122 (best seen in FIGS. 1, 8 and 9) or a variable angled opening 124 (best seen in FIGS. 8 and 9). That is, as will be appreciated by one of ordinary skill in the art, locking screw openings 122 may include a plurality of threads formed on an inner surface thereof for mating with threads formed on an outer surface of a head portion of a bone fixation device. Thus arranged, the bone fixation device may be said to be locked to the bone plate 100 via the locking screw openings 122. That is, as will be appreciated by one of ordinary skill in the art, the bone fixation device is threaded through one of the locking screw openings 122 formed in the bone plate 100 and into the patient's bone. The bone fixation device is secured to the bone plate 100 via threads formed on the head portion of the bone fixation device that cooperate with the threaded locking screw opening 122 formed in the bone plate 100. This secures the bone plate 100 with respect to the patient's bone and provides rigid fixation between the bone plate 100 and the bone fixation devices. That is, because the head portion of the bone fixation device interdigitates with the threads formed in the locking screw openings 122 of the bone plate 100, the plate 100 and the bone fixation devices form a stable system or construct, and the stability of the fracture can be dependent on or aided by the stiffness of the construct. Locking a bone fixation device into the bone plate 100 can achieve angular and axial stability and eliminate the possibility for the bone fixation device to toggle, slide, or be dislodged, reducing the risk of postoperative loss of reduction.

As previously mentioned, the bone fixation openings 120 may also be in the form of a variable angled opening 124 formed therein for receiving a non-locking or variable angled (e.g., polyaxial) bone fixation device. In use, the variable angled openings 124 are arranged and configured to enable the bone fixation device inserted therein to achieve a greater range of insertion angles as compared to, for example, a conventional locking bone fixation device (e.g., a locking screw 123) that is threadably coupled to the bone plate 100. For example, in one embodiment, the angular position of the bone fixation device may be rotated through a range of approximately ±15 degrees, although the range of allowable polyaxial rotation can vary, including greater and less than the fifteen degrees. In use, the variable angled openings 124 may be provided in any suitable manner, configuration, etc. now known or hereafter developed for enabling polyaxial positioning or angling of the bone fixation device relative to the bone plate 100.

Figure 8:
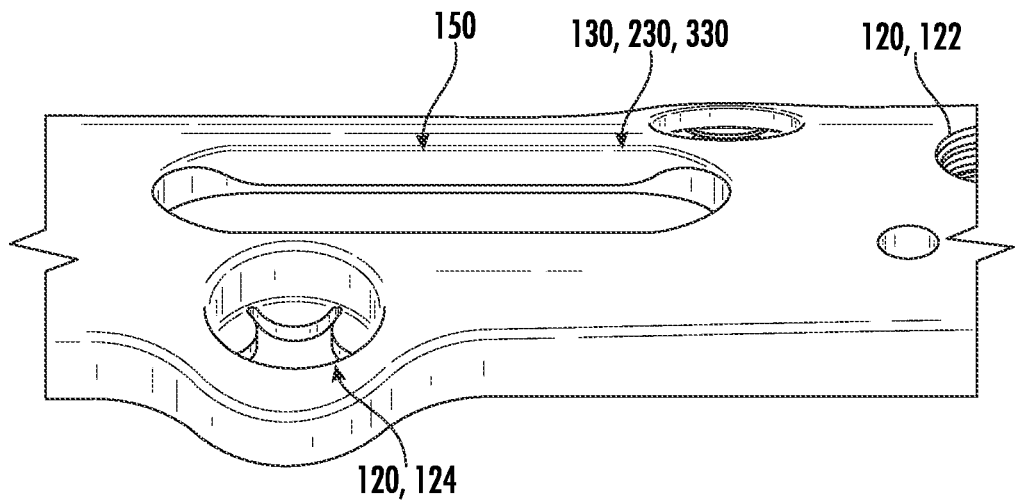
FIG. 8 illustrates a perspective view of an example embodiment of the elongate slot.
Figure 9:
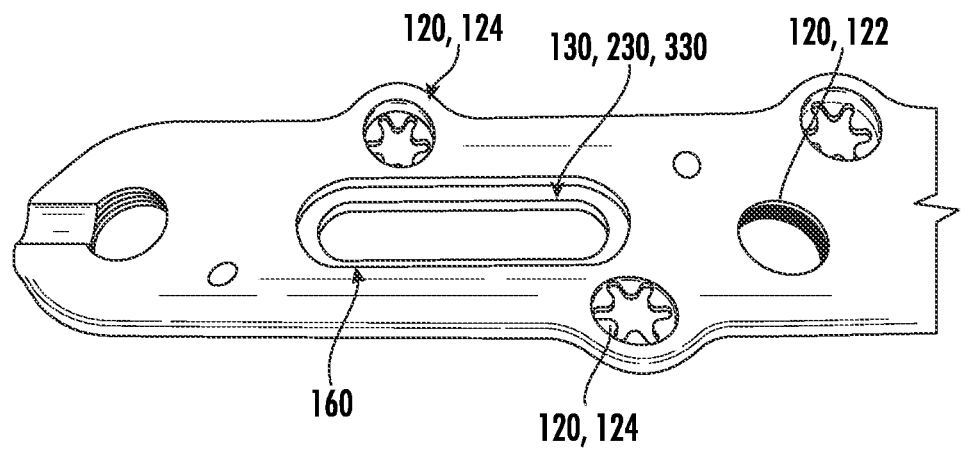
FIG. 9 illustrates a bottom view of the elongate slot shown in FIG. 8.

In one embodiment (as best illustrated in FIGS. 8 and 9), the variable angled openings 124 may include a plurality of fins or projections that extend radially inward from an inner surface of the variable angled openings 124 and into an interior region of the variable angled openings 124, and which are configured to engage or cooperate with the head portion of the bone fixation device. In use, the fins or projections engage the head portion of the bone fixation device in order to secure the bone fixation device at a desired position and at a desired angular orientation within the variable angled opening 124. Additional information on the operation and configuration of the fins can be found in U.S. patent application Ser. No. 15/706,877, with an earliest filing date of Jul. 25, 2005, now U.S. Pat. No. 10,092,337 entitled "Systems and Methods for Using Polyaxial Plates"; U.S. patent application Ser. No. 13/524,506, filed on Jun. 15, 2012, entitled "Variable Angle Locking Implant", and U.S. Patent Application No. 62/858,727, filed on June 7, entitled "Orthopedic Implant with Improved Variable Angle Locking Mechanism", the entire contents of which are hereby incorporated by reference.

As illustrated, in some embodiments, the bone plate 100 may also include one or more provisional fixation holes 140. As illustrated, in the embodiment depicted in FIG. 1, eight provisional fixation holes 140 are shown but as will be appreciated by one of ordinary skill in the art, the bone plate 100 may include any number of provisional fixation holes.

Figure 4:
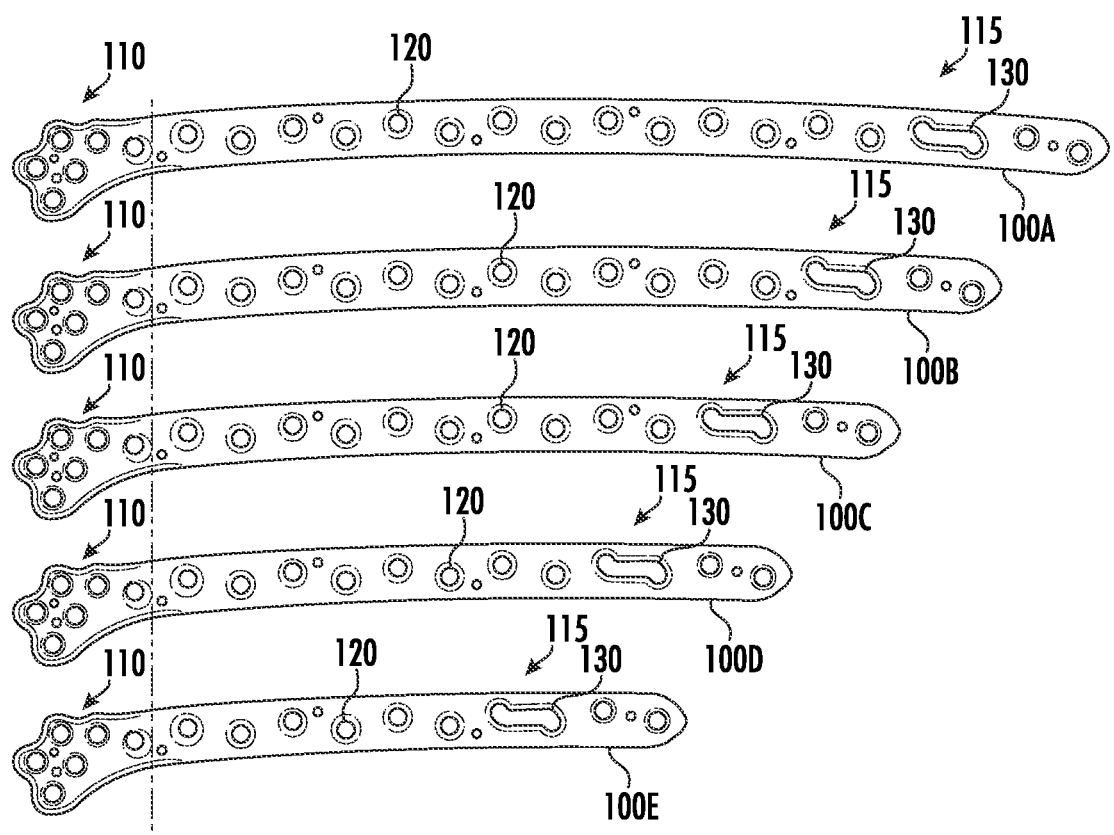
FIG. 4 illustrates the bone plate shown in FIG. 1 in various size configurations.

Referring to FIG. 4, the bone plate 100 may be provided in various sizes. For example, bone plate 100A may include nineteen (19) bone fixation openings 120 formed in the shaft portion 115 of the bone plate 100. Bone plate 100B may include seventeen (17) bone fixation openings 120 formed in the shaft portion 115, bone plate 100C may include sixteen (16) bone fixation openings 120 formed in the shaft portion 115, bone plate 100D may include thirteen (13) bone fixation openings 120 formed in the shaft portion 115, and bone plate 100E may include eleven (11) bone fixation openings 120 formed in the shaft portion 115. FIG. 4 is merely exemplary, and those of ordinary skill in the art will understand that any length of the bone plate and any number of bone fixation openings 120 may be used. In addition, the bone plate 100 may include any number of bone fixation openings 120 provided in any configuration of locking screw openings 122 and variable angled openings 124, which may be dependent on the length of the bone plate 100 and/or location of intended use.

As illustrated, and in accordance with one or more features of the present disclosure, the bone plate 100 includes a length adjusting elongate hole 130. As will be described herein, in use, the length adjusting elongate hole 130 is arranged and configured to receive a bone fixation device such as for example, a bone screw, a fastener, or other compression device. The length adjusting elongate hole 130 may be provided in any suitable length. In addition, although the bone plate 100 is shown and described as including a single length adjusting elongate hole, the bone plate may include more than one length adjusting elongate hole such as, for example, two, three, or more.

In use, in accordance with one or more features of the present disclosure, the bone fixation device positioned within the length adjusting elongate hole 130 may be initially secured or tightened to the patient's underlying fractured bone. Thereafter, the bone fixation device may be partially loosened without removal to enable the patient's bone to be adjusted (e.g., loosening the bone fixation device within the length adjusting elongate hole 130 allows the surgeon to adjust the position of the bone fixation device relative to the bone plate 100 and hence the position of the patient's bone). Once properly adjusted, the bone fixation device positioned within the length adjusting elongate hole 130 may be retightened.

Figure 5:
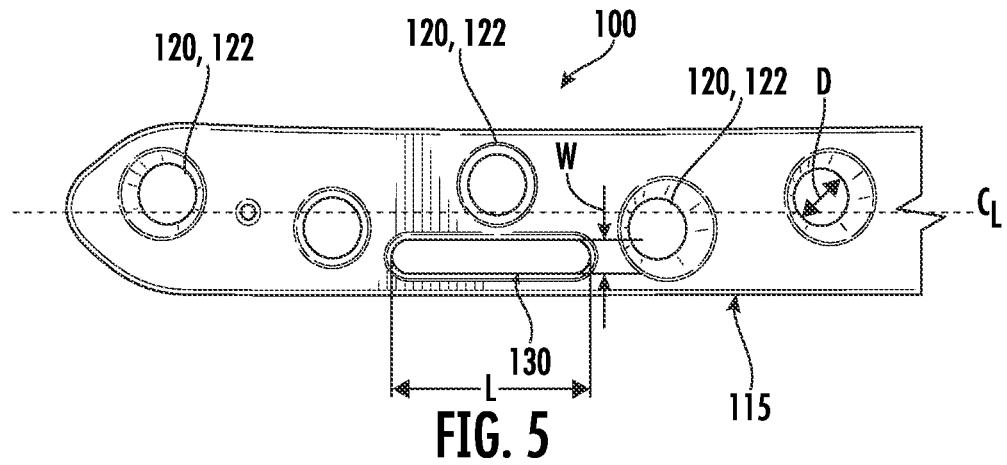
FIG. 5 illustrates a top view of an example embodiment of an elongate slot that may be incorporated into the bone plate of FIG. 1 in accordance with one or more features of the present disclosure.

Referring to FIG. 5, a first example embodiment of a length adjusting elongate hole 130 is shown. In the depicted embodiment, the central longitudinal axis of the elongate hole 130 may be positioned offset or a distance from the central longitudinal axis CL of the shaft portion 115 of the bone plate 100. Thus arranged, in one embodiment, as illustrated, the elongate hole 130 may be positioned adjacent to and offset from a bone fixation opening 120 formed in the bone plate 100 such as, for example, a locking screw opening 122. As such, incorporation of the elongate hole 130 does not sacrifice, eliminate, or prevent a surgeon from using a bone fixation opening (e.g., bone plate 100 may include same configuration and number of bone fixation openings 120 regardless of the inclusion of the length adjusting elongate hole 130. Moreover, placement of the bone fixation device within the length adjusting elongate hole 130 does not preclude a surgeon from using any of the other bone fixation openings 120 formed in the bone plate 100).

Thus arranged, in use, a bone fixation device may be inserted into the elongate hole 130 to provisionally couple an end of the bone plate 100 to the patient's underlying fractured bone. Thereafter, adjustment to the underlying bone may be performed by the surgeon. The underlying bone can be compressed or distracted as needed. Upon proper positioning of the underlying bone, additional bone fixation devices may be inserted into the bone fixation openings 120 including the bone fixation opening positioned adjacent to and offset from the elongate hole 130. As such, incorporation of the elongate opening 130 does not sacrifice or limit the availability of any bone fixation openings during the surgical procedure.

In one embodiment, the elongate hole 130 is arranged and configured so that a bone fixation device may be positioned and locked anywhere along a length of the elongate hole 130 thus facilitating both compression and distraction. In some embodiments, the elongate hole 130 has a length L at least twice the diameter D of a bone fixation opening 120 formed in the bone plate 100 such as, for example, a locking screw opening 122 (e.g., the length L may be equal to the spacing of the plurality of bone fixation openings 120 formed in the shaft portion 115 of the bone plate 100). In addition, the elongate hole 130 may include a width W sized to accept a bone fixation device. Thus arranged, in use, a bone fixation device can be locked within the elongate hole 130. In the depicted embodiment, the width W of the elongate hole 130 is sized to accept the shaft of a cortical bone screw.

Figure 6:
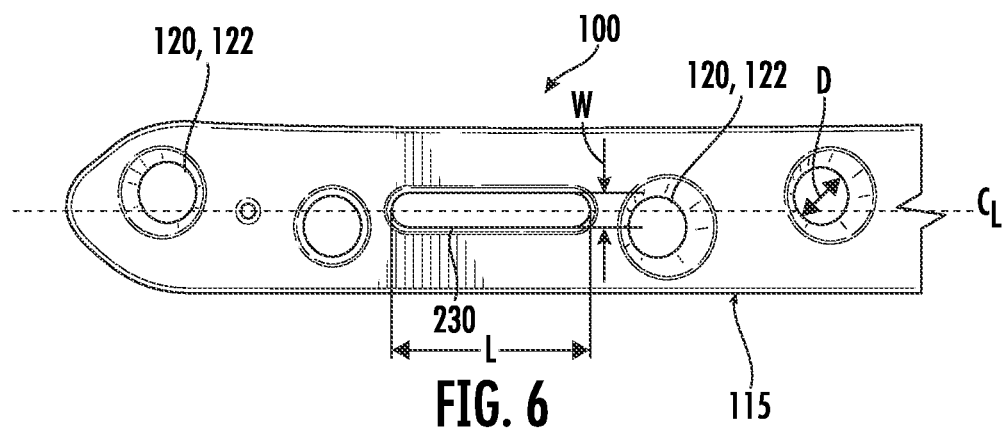
FIG. 6 illustrates a top view of another example embodiment of an elongate slot that may be incorporated into the bone plate of FIG. 1 in accordance with one or more features of the present disclosure.

Referring to FIG. 6, an alternate embodiment of a bone plate 100 including a length adjusting elongate hole 230 is illustrated. In the depicted embodiment, the central longitudinal axis of the length adjusting elongate hole 230 is positioned generally along (e.g., aligned with) the central longitudinal axis of the shaft portion 115 of the bone plate 100. In use, as illustrated, the elongate hole 230 may include a length L arranged and configured to be positioned between adjacent bone fixation openings 120. In addition, the elongate hole 230 may include a width W sized to accept a provisional fixation pin. In use, the size (e.g., diameter) of the provisional fixation pin may be less than or smaller than the size of any starter hole used to install a bone fixation device. Thus arranged, in use, a provisional bone fixation pin may be inserted into the elongate hole 230. Thereafter, adjustment to the underlying bone may be performed by the surgeon. The underlying bone can be compressed or distracted as needed. Upon proper positioning of the underlying bone, if the underlying bone is adjusted to such an extent that a bone fixation opening now aligns with the hole formed for the provisional bone fixation pin, a bone fixation device can be inserted into the hole formed in the patient's bone. As such, incorporation of the elongate opening 230 does not sacrifice, eliminate, or prevent a surgeon from using a bone fixation opening.

In one embodiment, the elongate hole 230 is arranged and configured so that a bone fixation device may be positioned and locked anywhere along a length of the elongate hole 230 thus facilitating both compression and distraction. In some embodiments, the elongate hole 230 may include a length L of at least twice the diameter D of the bone fixation opening 120 formed in the bone plate 100 such as, for example, a locking screw opening 122. In addition, the elongate hole 230 may include a width W sized to accept a bone fixation device. Thus arranged, in use, a bone fixation device can be locked within the elongate hole 230. In the depicted embodiment, the width W of the elongate hole 130 is sized to accept the shaft of a cortical bone screw.

Figure 7:
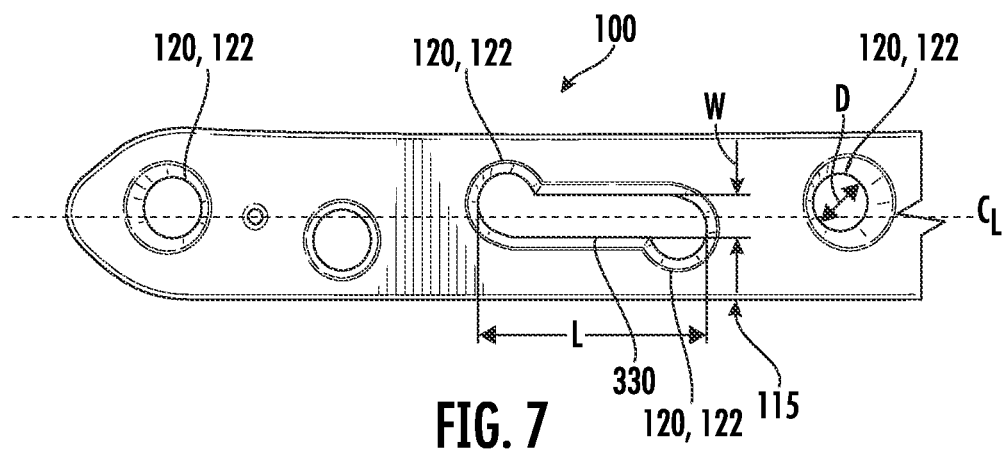
FIG. 7 illustrates a top view of another example embodiment of an elongate slot that may be incorporated into the bone plate of FIG. 1 in accordance with one or more features of the present disclosure.

Referring to FIG. 7, an alternate embodiment of a bone plate 100 including a length adjusting elongate hole 330 is illustrated. In the depicted embodiment, the central longitudinal axis of the length adjusting elongate hole 330 is positioned generally along (e.g., aligned with) the central longitudinal axis of the shaft portion 115 of the bone plate 100. As illustrated, the length adjusting elongate hole 330 may run or be in communication with adjacent pairs of bone fixation openings 120. As such, in use, a locking screw opening 122 may be positioned on either side of the length adjusting elongate hole 330. Thus arranged, dual side locking of a bone fixation device within the length adjusting elongate hole 330 is enabled thus facilitating both compression and distraction. In one embodiment, the length adjusting elongate hole 330 is arranged and configured so that a bone fixation device may be positioned and locked anywhere along a length of the length adjusting elongate hole 330 thus facilitating both compression and distraction.

Moreover, as illustrated in FIG. 7, the bone fixation openings 120 such as the locking screw openings 122 may be mirror offset from one another (e.g., positioned slightly on either side of the central longitudinal axis of the shaft portion 115 of the bone plate 100).

Thus arranged, incorporation of the length adjusting elongate opening 330 does not sacrifice, eliminate, or prevent a surgeon from using a bone fixation opening (e.g., incorporation of the length adjusting elongate hole 330 does not replace a locking screw opening or preclude a surgeon from using any of the locking screw openings 122 during the surgical procedure). In use, a bone fixation device may be inserted into the length adjusting elongate hole 330. Thereafter, adjustment to the underlying bone may be performed by the surgeon. The underlying bone can be compressed or distracted as needed. Upon proper positioning of the underlying bone, the initial bone fixation device may be positioned within one of the bone fixation openings 120 in communication with the length adjusting elongate hole 330. Alternatively, an additional bone fixations device may be inserted into one of the bone fixation openings 120 in communication with the length adjusting elongate hole 330. As such, incorporation of the elongate opening 330 does not sacrifice any bone fixation openings.

In some embodiments, the elongate hole 330 has a length L of at least twice the diameter D of the bone fixation opening 120 formed in the bone plate 100 such as, for example, a locking screw opening 122 (e.g., the length L may be equal to the spacing of the plurality of bone fixation openings 120 formed in the shaft portion 115 of the bone plate 100). In addition, the elongate hole 330 may include a width W sized to accept a bone fixation device. Thus arranged, in use, a bone fixation device can be locked within the elongate hole 330. In the depicted embodiment, the width W of the elongate hole 130 is sized to accept the shaft of a cortical bone screw.

In some embodiments, referring to FIG. 8, the length adjusting elongate hole 130, 230, 330 may include a dished or recessed region 150 on the upper surface 104 of the bone plate 100. In the embodiment depicted in FIG. 8, the dished region 150 generally extends along a longitudinal portion of the elongate hole 130, 230, 330. In some embodiments, referring to FIG. 9, the elongate hole 130, 230, 330 may include a recess 160 on the bone-facing surface 102 of the bone plate 100. In the embodiment depicted in FIG. 9, the recess 160 is spaced apart from the bone facing surface 102 and is generally planar. In use, the recess 160 provides additional clearance between the underlying bone and the elongate hole 130, 230, 330 to facilitate use of large diameter bone fixation devices.

Referring to FIGS. 8 and 9, the variable angled openings 124 formed in the shaft portion 115 of the bone plate 100 may be positioned along and/or adjacent to an outer periphery or surface 106 of the shaft portion 115 of the bone plate 100 (e.g., the variable angled openings 124 may be positioned closer to the outer periphery 106 of the bone plate 100 as compared to the locking screw openings 122, which may be more centrally located and substantially along the central longitudinal axis CL of the shaft portion 115). Thus arranged, incorporation of the length adjusting elongate hole 130, 230, 330 does not sacrifice or prevent incorporation of additional locking screw openings 122.

Figure 10:
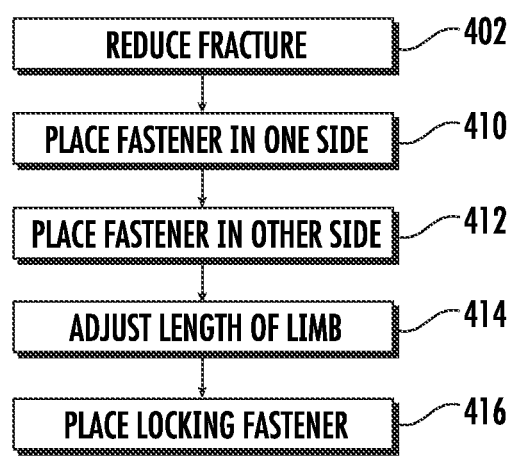
FIG. 10 illustrates a block diagram of an example embodiment of a surgical method in accordance with one or more features of the present disclosure.

Referring to FIG. 10, an example embodiment of a surgical method 400 is also disclosed. In a first step 402, the bone fracture may be reduced. For example, reduction may be accomplished through manual manipulation of the patient's bone. In a second step 410, a bone fixation device may be inserted through the bone plate 100 and into the patient's bone, the bone fixation device may be positioned on one side of the patient's fracture line. For example, a cortical bone screw may be inserted in the length adjusting elongate hole 130, 230, 330 and provisionally holds the bone plate 100 to the patient's bone. In a third step 412, a bone fixation device may be inserted into one of the plurality of bone fixation openings 120 formed in the bone plate 100. The bone fixation device securing the other side of the bone plate 100 to the patient's bone. The bone fixation device being positioned on the other side of the bone fracture line. Alternatively, however, the first bone fixation device may be coupled to one of the plurality of bone fixation openings 120 and the second bone fixation device may be inserted into the length adjusting elongate hole 130, 230, 330.

Next, the length of the patient's bone (e.g., limb) may be adjusted. The adjustment may be either compression or distraction. In some embodiments, the provisional compression of the bone fixation device through the length adjusting elongate hole 130, 230, 330 may be reduced before adjustment. In some embodiments, the bone plate 100 may be compressed back down to the patient's bone using the previously inserted bone fixation device positioned in the length adjusting elongate hole 130, 230, 330 after length adjustment. Finally, one or more additional locking screws may be inserted into one or more bone fixation openings 120 adjacent to the length adjusting elongate hole 130, 230, 330.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

What is claimed is:

1. A bone plate comprising:
   a shaft portion including a central longitudinal axis, an upper surface, a bottom surface, and a plurality of bone fixation openings extending between the upper and bottom surfaces, each of the plurality of bone fixation openings being arranged and configured to receive a bone fixation device for coupling the bone plate to a patient's bone; and
   a length adjusting elongate hole formed in the shaft portion, the length adjusting elongate hole including a central longitudinal axis, the length adjusting elongate hole arranged and configured to enable a length of the patient's bone to be adjusted without requiring the bone plate to be completely decoupled from the patient's bone;
   wherein the central longitudinal axis of the length adjusting elongate hole is aligned with the central longitudinal axis of the shaft portion, the length adjusting elongate hole extending between adjacent bone fixation openings formed in the shaft portion of the bone plate so that the length adjusting elongate hole is in communication with the adjacent bone fixation openings;
   wherein the adjacent bone fixation openings are a first locking screw opening and a second locking screw opening;
   wherein the first and second locking screw openings each comprise, respectively, a central longitudinal axis;
   wherein the central longitudinal axis of the first locking screw opening and the central longitudinal axis of the second locking screw opening both extend parallel to the central longitudinal axis of the shaft portion; and
   wherein the central longitudinal axis of the first locking screw openings is positioned on an opposite side of the central longitudinal axis of the shaft portion from the central longitudinal axis of the second locking screw opening.

2. The bone plate of claim 1, wherein the length adjusting elongate hole includes a length at least twice a diameter of a bone fixation opening.

3. The bone plate of claim 1, wherein the length adjusting elongate hole includes a dished or recessed region arranged and configured to enable a bone fixation device to be recessed relative to the upper surface of the bone plate.

4. The bone plate of claim 3, wherein the length adjusting elongate hole includes a recess portion on the bottom surface.

5. A method of fracture reduction utilizing a bone plate with a length adjusting elongate hole formed in a shaft portion of the bone plate, the method comprising:
   coupling a portion of the bone plate to a patient's bone utilizing one or more bone fixation devices;
   inserting a bone fixation device into the length adjusting elongate hole, the bone fixation device being positioned within one side of the length adjusting elongate hole;
   reducing an amount of provisional compression from the bone fixation device;
   adjusting a length of the patient's bone;
   compressing the bone plate against the patient's bone using the previously inserted bone fixation device; and
   inserting a locking screw into an adjacent locking screw opening formed in the bone plate;
   wherein a central longitudinal axis of the length adjusting elongate hole is aligned with a central longitudinal axis of the bone plate, the length adjusting elongate hole extending between adjacent bone fixation openings formed in the bone plate so that the length adjusting elongate hole is in communication with the adjacent bone fixation openings;
   wherein the adjacent bone fixation openings are a first locking screw opening and a second locking screw opening;
   wherein the first and second locking screw openings each comprise, respectively, a central longitudinal axis;
   wherein the central longitudinal axis of the first locking screw opening and the central longitudinal axis of the second locking screw opening both extend parallel to the central longitudinal axis of the shaft portion; and
   wherein the central longitudinal axis of the first locking screw openings are is positioned on an opposite side of the central longitudinal axis of the shaft portion from the central longitudinal axis of the second locking screw opening.

6. The method of claim 5, wherein the bone plate is provisionally held against the patient's bone during inserting the bone fixation device into the length adjusting elongate hole.

7. The method of claim 5, wherein adjusting a length of the patient's bone comprises reducing or compressing the patient's bone.

8. The method of claim 5, wherein adjusting a length of the patient's bone comprises lengthening or distracting the patient's bone.

9. The method of claim 8, further comprising reducing the patient's bone.

10. The method of claim 9, wherein reducing the patient's bone is accomplished prior to coupling a portion of the bone plate to the patient's bone.

11. The method of claim 5, wherein the length adjusting elongate hole includes a length at least twice a diameter of a bone fixation opening.

12. The method of claim 5, wherein the length adjusting elongate hole includes a dished or recessed region arranged and configured to enable a bone fixation device to be recessed relative to the upper surface of the bone plate.

13. The method of claim 5, wherein the length adjusting elongate hole includes a recess portion on the bottom surface.

* * * * *